United States Patent
Dinges et al.

(10) Patent No.: US 11,364,033 B2
(45) Date of Patent: Jun. 21, 2022

(54) MEDICAL DEVICE RELEASE SYSTEM

(71) Applicant: BOSTON SCIENTIFIC SCIMED, INC., Maple Grove, MN (US)

(72) Inventors: Eric Dinges, Edina, MN (US); Nicholas Lee Tassoni, Andover, MN (US); Kevin McConnell, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 219 days.

(21) Appl. No.: 16/280,104

(22) Filed: Feb. 20, 2019

(65) Prior Publication Data

US 2019/0254678 A1 Aug. 22, 2019

Related U.S. Application Data

(60) Provisional application No. 62/632,503, filed on Feb. 20, 2018.

(51) Int. Cl.
*A61B 17/12* (2006.01)
*A61B 17/00* (2006.01)
(Continued)

(52) U.S. Cl.
CPC .. *A61B 17/12022* (2013.01); *A61B 17/12109* (2013.01); *A61B 90/92* (2016.02);
(Continued)

(58) Field of Classification Search
CPC ...... A61B 17/12022; A61B 2017/1205; A61B 2017/00477; A61B 17/12109;
(Continued)

(56) References Cited

U.S. PATENT DOCUMENTS

| 5,261,916 A | 11/1993 | Engelson |
| 5,304,195 A | 4/1994 | Twyford, Jr. et al. |

(Continued)

FOREIGN PATENT DOCUMENTS

| CN | 202497189 U | 10/2012 |
| EP | 0832607 A1 | 4/1998 |

(Continued)

OTHER PUBLICATIONS

International Search Report and Written Opinion dated Jun. 6, 2019 for International Application No. PCT/US2019/018682.
(Continued)

*Primary Examiner* — Kathleen S Holwerda
*Assistant Examiner* — Uyen N Vo
(74) *Attorney, Agent, or Firm* — Seager, Tufte & Wickhem LLP

(57) ABSTRACT

A medical device system may include an elongate shaft having a lumen extending from a proximal end to a distal end, a release wire disposed within the lumen of the elongate shaft configured to releasably attach a medical device to the distal end of the elongate shaft, and a securement member releasably coupled to the proximal end of the elongate shaft and fixedly attached to a proximal end of the release wire. A proximal portion of the securement member may be configured to translate proximally away from the proximal end of the elongate shaft upon application of a proximally-directed force to the proximal portion of the securement member and radially inward directed force to the distal portion of the securement member while the elongate shaft is maintained in a fixed position.

15 Claims, 10 Drawing Sheets

(51) Int. Cl.
*A61B 90/92* (2016.01)
*A61F 2/95* (2013.01)

(52) U.S. Cl.
CPC .......... *A61B 2017/0042* (2013.01); *A61B 2017/00367* (2013.01); *A61B 2017/00477* (2013.01); *A61B 2017/00893* (2013.01); *A61B 2017/00911* (2013.01); *A61B 2017/1205* (2013.01); *A61B 2017/12054* (2013.01); *A61F 2/95* (2013.01)

(58) Field of Classification Search
CPC ....... A61B 2017/12054; A61B 17/3468; A61F 2/95; A61F 2002/9505; A61F 2002/9511; A61F 2002/9528; A61F 2002/9534
See application file for complete search history.

(56) References Cited

U.S. PATENT DOCUMENTS

| | | | |
|---|---|---|---|
| 5,350,397 A | 9/1994 | Palermo et al. | |
| 5,800,454 A | 9/1998 | Jacobsen et al. | |
| 5,853,418 A | 12/1998 | Ken et al. | |
| 5,891,058 A | 4/1999 | Taki et al. | |
| 5,891,130 A | 4/1999 | Palermo et al. | |
| 5,895,391 A | 4/1999 | Farnholtz | |
| 6,551,340 B1 | 4/2003 | Konya et al. | |
| 8,333,796 B2 | 12/2012 | Tompkins et al. | |
| 9,186,151 B2 | 11/2015 | Tompkins et al. | |
| 9,554,805 B2 | 1/2017 | Tompkins et al. | |
| 9,615,951 B2 | 4/2017 | Bennett et al. | |
| 2004/0111095 A1 | 6/2004 | Gordan et al. | |
| 2005/0192621 A1 | 9/2005 | Wallace et al. | |
| 2006/0276832 A1 | 12/2006 | Balgobin et al. | |
| 2007/0135826 A1* | 6/2007 | Zaver | A61B 17/12022 606/157 |
| 2007/0167981 A1 | 7/2007 | Opolski et al. | |
| 2007/0293928 A1 | 12/2007 | Tomlin | |
| 2008/0039743 A1 | 2/2008 | Fox et al. | |
| 2008/0097462 A1 | 4/2008 | Mitelberg et al. | |
| 2010/0030200 A1 | 2/2010 | Strauss et al. | |
| 2010/0174269 A1* | 7/2010 | Tompkins | A61B 17/1214 604/507 |
| 2012/0041470 A1* | 2/2012 | Shrivastava | A61B 17/1219 606/200 |
| 2012/0330348 A1* | 12/2012 | Strauss | A61B 17/12154 606/200 |
| 2013/0331882 A1 | 12/2013 | Tompkins et al. | |
| 2016/0008003 A1* | 1/2016 | Kleshinski | A61B 17/12031 606/200 |

FOREIGN PATENT DOCUMENTS

| | | |
|---|---|---|
| EP | 1728477 A1 | 12/2006 |
| EP | 1797833 A1 | 6/2007 |
| EP | 1813213 A2 | 8/2007 |
| EP | 2777542 A2 | 9/2014 |
| WO | 9311719 A1 | 6/1993 |
| WO | 9311825 A1 | 6/1993 |
| WO | 9406502 A2 | 3/1994 |
| WO | 03002018 A1 | 1/2003 |
| WO | 2007070792 A2 | 6/2007 |
| WO | 2007070797 A2 | 6/2007 |
| WO | 2007121405 A2 | 10/2007 |
| WO | 2018022186 A1 | 2/2018 |

OTHER PUBLICATIONS

Office Action dated Jun. 17, 2016 for U.S. Appl. No. 14/460,234.
Office Action dated Oct. 6, 2015 for U.S. Appl. No. 14/460,234.
Office Action dated Oct. 7, 2014 for U.S. Appl. No. 14/460,234.
Office action dated May 15, 2015 for U.S. Appl. No. 14/460,234.

* cited by examiner

MEDICAL DEVICE RELEASE SYSTEM

CROSS-REFERENCE TO RELATED APPLICATIONS

This application claims the benefit of priority under 35 U.S.C. § 119 to U.S. Provisional Application Ser. No. 62/632,503, filed Feb. 20, 2018, the entirety of which is incorporated herein by reference.

TECHNICAL FIELD

The present disclosure pertains to medical devices and methods for manufacturing and/or using medical devices. More particularly, the present disclosure pertains to configurations of a system for releasing medical implants.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first example, a medical device system may comprise an elongate shaft having a lumen extending from a proximal end of the elongate shaft to a distal end of the elongate shaft, at least one slot extending from an inner surface to an outer surface of the elongate shaft adjacent to the proximal end of the elongate shaft, a release wire disposed within the lumen of the elongate shaft, wherein the release wire is configured to releasably attach a medical device to the distal end of the elongate shaft, and a securement member having a proximal portion and a distal portion, the proximal portion fixedly secured to a proximal end of the release wire and the distal portion having at least one clip movable between an expanded configuration and a compressed configuration and releasably coupled within the at least one slot of the elongate shaft. The securement member may be configured to translate proximally away from the proximal end of the elongate shaft upon application of a proximally-directed force to the proximal portion of the securement member and upon movement of the at least one clip to the compressed configuration while the elongate shaft is maintained in a fixed position.

Alternatively or additionally to any of the examples above, in another example, the movement of the at least one clip to the compressed configuration may be an application of a radially inward directed force to the at least one clip.

Alternatively or additionally to any of the examples above, in another example, the radially inward directed force to the at least one clip may be applied by an operator.

Alternatively or additionally to any of the examples above, in another example, the radially inward directed force to the at least one clip may be applied by an inner surface of the elongate shaft.

Alternatively or additionally to any of the examples above, in another example, the at least one clip may include a proximal portion and a distal interlocking portion.

Alternatively or additionally to any of the examples above, in another example, the distal interlocking portion of the at least one clip may be configured to be positioned within the at least one slot.

Alternatively or additionally to any of the examples above, in another example, when in the expanded configuration at least a portion of the distal interlocking portion of the at least one clip may have a radial dimension greater than an inner diameter of the elongate shaft.

Alternatively or additionally to any of the examples above, in another example, when in the compressed configuration, the distal interlocking portion of the at least one clip may have a radial dimension substantially equal to or less than an inner diameter of the elongate shaft.

Alternatively or additionally to any of the examples above, in another example, the distal interlocking portion of the at least one clip may include a distally tapering surface.

Alternatively or additionally to any of the examples above, in another example, the distal interlocking portion of the at least one clip may include a proximally tapering surface.

Alternatively or additionally to any of the examples above, in another example, the at least one slot may comprise a first slot and a second slot positioned circumferentially opposite the first slot.

Alternatively or additionally to any of the examples above, in another example, the at least one clip may comprise a first clip and a second clip.

Alternatively or additionally to any of the examples above, in another example, proximal translation of the proximal portion of the securement member away from the proximal end of the elongate shaft may translate the release wire axially relative to the elongate shaft.

Alternatively or additionally to any of the examples above, in another example, the medical device system may further comprise a medical device disposed proximate the distal end of the elongate shaft, wherein the release wire releasably secures the medical device to the distal end of the elongate shaft; and a microcatheter configured to deliver the medical device to a treatment site, the elongate shaft and the medical device being slidably disposed within a lumen of the microcatheter.

Alternatively or additionally to any of the examples above, in another example, the elongate shaft may include a first portion of a release mechanism attached to the distal end of the elongate shaft and the medical device may include a second portion of the release mechanism attached to a proximal end of the medical device. The release wire may interlock the first portion of the release mechanism with the second portion of the release mechanism when the proximal portion of the securement member is biased distally by the distal portion of the securement member.

In another example a medical device system may comprise an elongate shaft having a lumen extending from a proximal end of the elongate shaft to a distal end of the elongate shaft, a first slot and a second slot positioned circumferentially opposite from the first slot, the first and second slots each extending from an inner surface to an outer surface of the elongate shaft adjacent to the proximal end of the elongate shaft, a release wire disposed within the lumen of the elongate shaft, wherein the release wire is configured to releasably attach a medical device to the distal end of the elongate shaft, and a securement member. The securement member may comprise a proximal portion fixedly secured to a proximal end of the release wire, a first clip extending distally from the proximal portion and releasably coupled with the first slot, and a second clip extending distally from the proximal portion and releasably coupled with the second slot.

The first and second clips may be movable between an expanded configuration and a compressed configuration. The securement member may be configured to translate proximally away from the proximal end of the elongate shaft upon application of a proximally-directed force to the proximal portion of the securement member and upon movement of the first and second clips to the compressed configuration while the elongate shaft is maintained in a fixed position.

Alternatively or additionally to any of the examples above, in another example, when the first and second clips are releasably coupled with the first and second slots, the release wire may be axially and rotatably secured relative to the elongate shaft.

Alternatively or additionally to any of the examples above, in another example, when the first and second clips are disengaged from the first and second slots, the release wire may be axially and rotatably movable relative to the elongate shaft.

Alternatively or additionally to any of the examples above, in another example, proximal translation of the proximal portion of the securement member away from the proximal end of the elongate shaft may translate the release wire axially relative to the elongate shaft.

Alternatively or additionally to any of the examples above, in another example, the elongate shaft may include a first portion of a release mechanism attached to the distal end of the elongate shaft and the medical device may include a second portion of the release mechanism attached to a proximal end of the medical device. The release wire may interlock the first portion of the release mechanism with the second portion of the release mechanism when the proximal portion of the securement member may be biased distally by a distal portion of the securement member.

In another example, a method of delivering a medical device to a treatment site may comprise inserting a microcatheter into a patient's anatomy and guiding a distal end of the microcatheter to a location adjacent the treatment site and inserting a medical device disposed at a distal end of an elongate shaft into a proximal end of a lumen disposed within the microcatheter. The medical device may be releasably attached to the distal end of the elongate shaft by a pull wire extending through a lumen within the elongate shaft, and a securement member may extend proximally from the elongate shaft, the securement member being releasably coupled to the elongate shaft and fixedly attached to the pull wire The method may further comprise advancing the medical device through the microcatheter to the treatment site and uncoupling the securement member from the elongate shaft with an applied radially inward directed force and substantially simultaneous to the radially inward force translating a proximal portion of the securement member proximally away from a proximal end of the elongate shaft while the elongate shaft is maintained in a fixed position to translate the pull wire relative to the elongate shaft, thereby releasing the medical device from the elongate shaft.

Alternatively or additionally to any of the examples above, in another example, the proximal portion of the securement member may be fixedly attached to the pull wire and a distal portion of the securement member may be releasably coupled to the elongate shaft.

Alternatively or additionally to any of the examples above, in another example, a first portion of a release mechanism may be attached to the distal end of the elongate shaft and a second portion of the release mechanism may be attached to a proximal end of the medical device.

Alternatively or additionally to any of the examples above, in another example, the pull wire may be slidably disposed within the elongate shaft, the first portion of the release mechanism, and the second portion of the release mechanism.

Alternatively or additionally to any of the examples above, in another example, the applied radially inward directed force may move a distal portion of the securement member from an expanded configuration having a radial dimension greater than an inner diameter of the elongate shaft to a compressed configuration having a radial dimension substantially equal to or less than the inner diameter of the elongate shaft.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
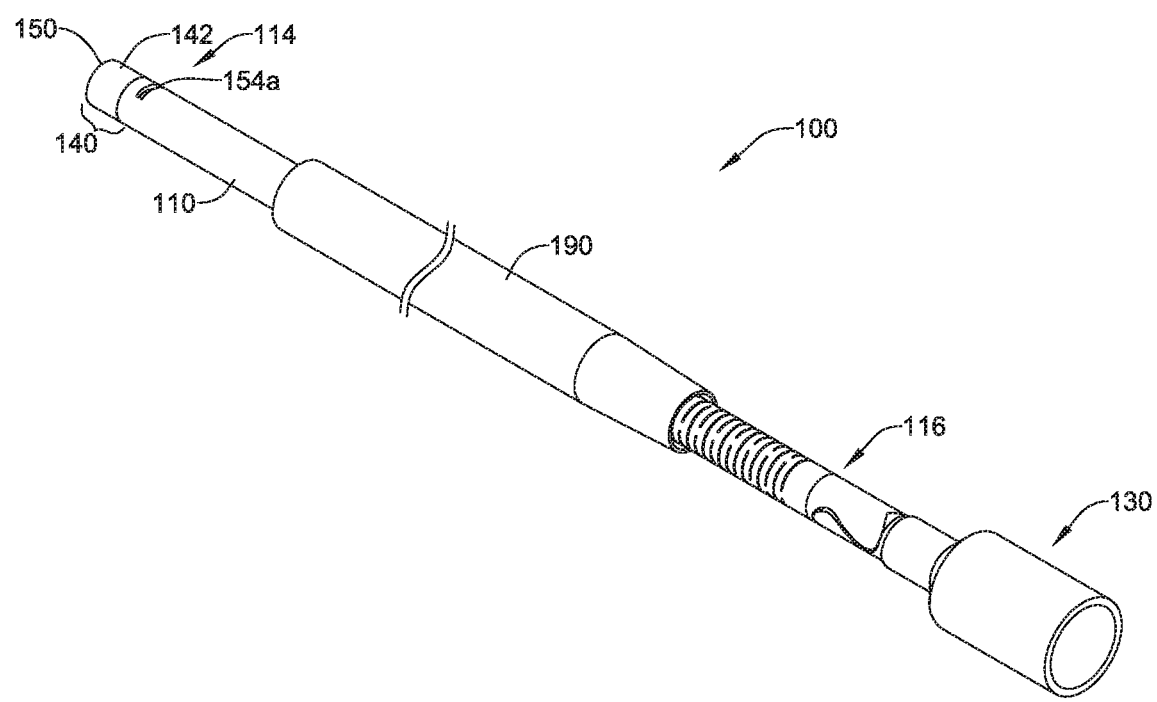
FIG. 1 is a perspective view of an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless specifically referred to as a minimum extent. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. However, where referred to as a "minimum extent", the "extent" shall refer to a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact and/or are affected by the cardiovascular system are prevalent throughout the world. For example, some forms of arterial venous malformations (AVMs) may "feed" off of normal blood flow through the vascular system. Without being bound by theory, it is believed that it may be possible to treat, at least partially, arterial venous malformations and/or other diseases or conditions by starving them of normal, oxygen and/or nutrient-rich blood flow, thereby limiting their ability to grow and/or spread. Other examples of diseases or conditions that may benefit from vascular occlusion include, but are not limited to, bleeds, aneurysms, venous insufficiency, shutting off blood flow prior to organ resection, or preventing embolic bead reflux into branch vessels in the liver. Disclosed herein are medical devices that may be used within a portion of the cardiovascular system in order to treat and/or repair some arterial venous malformations and/or other diseases or conditions. The devices disclosed herein may also provide a number of additional desirable features and benefits as described in more detail below.

Figure 2:
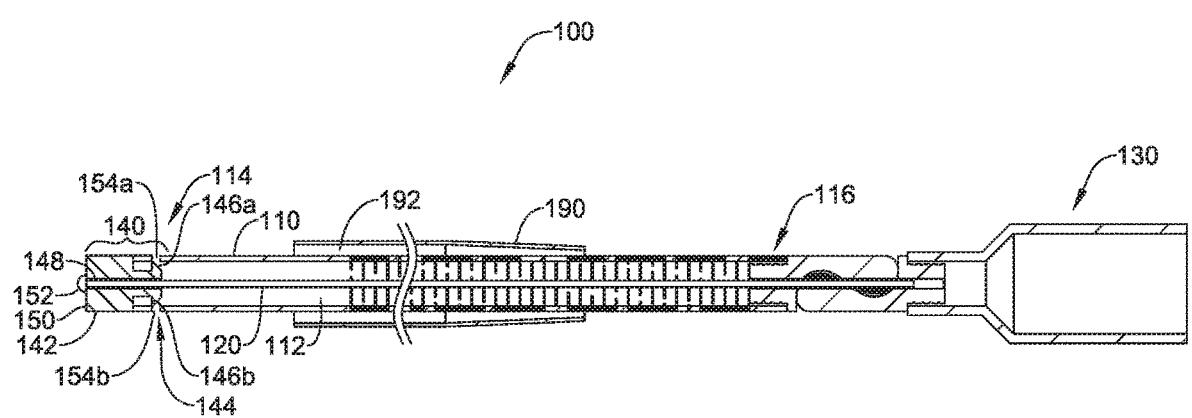
FIG. 2 is a partial cut-away view of an example medical device system.

FIGS. 1 and 2 illustrate aspects of an example medical device system 100. The medical device system 100 may include an elongate shaft 110 having a lumen 112 (e.g., FIG. 2) extending from a proximal end 114 of the elongate shaft 110 to a distal end 116 of the elongate shaft 110. In some embodiments, the elongate shaft 110 may be a catheter, a hypotube, or other similar tubular structure. In some embodiments, at least a portion of the elongate shaft 110 may include micromachining, a plurality of cuts or weakened areas, some degree of material removal, etc. to provide increased flexibility along a length of the elongate shaft 110 for navigating tortuous vasculature. Some suitable but non-limiting materials for the elongate shaft 110, for example metallic materials, polymer materials, composite materials, etc., are described below.

The medical device system 100 may include a release wire 120 (e.g., FIG. 2) slidably disposed within the lumen 112 of the elongate shaft 110. A medical device 130 may be disposed proximate the distal end 116 of the elongate shaft 110. The release wire 120 may be axially slidable between an interlocked position and a released position. The release wire 120 may be configured to releasably attach the medical device 130 to the distal end 116 of the elongate shaft 110. The medical device 130 may be configured to expand from a delivery configuration to a deployed configuration. For simplicity, the medical device 130 is illustrated herein as a vascular occlusion device, but other suitable medical devices transported, delivered, used, released, etc. in a similar manner are also contemplated, including but not limited to, embolic coils, stents, embolic filters, replacement heart valves, other occlusion devices, and/or other medical implants, etc. In some embodiments, the release wire 120 may be alternately and/or interchangeably referred to as a pull wire, an actuation wire, and/or a locking wire. The release wire 120 may generally be a solid wire or shaft, but may also be tubular in some embodiments. Some suitable but non-limiting materials for the release wire 120, for example metallic materials, polymer materials, composite materials, etc., are described below.

In some embodiments, the medical device system 100 may include a microcatheter 190 sized and configured to deliver the medical device 130 to a treatment site in a delivery configuration. The elongate shaft 110 and the medical device 130 may be slidably disposed within a lumen 192 (e.g., FIG. 2) of the microcatheter 190. In some embodiments, the microcatheter 190 may facilitate percutaneous delivery of the medical device 130 to the treatment site. For reference only, the medical device 130 may be shown in the figures (e.g., FIGS. 1-2 and 7-9) in the deployed configuration or an at least partially-deployed configuration. The skilled person will recognize that the medical device 130 may be radially constrained into the delivery configuration when the medical device 130 is disposed within the lumen 192 of the microcatheter 190. Some suitable but non-limiting materials for the microcatheter 190, for example metallic materials, polymer materials, composite materials, etc., are described below.

As seen in FIGS. 1 and 2, the medical device system 100 may include a securement member 140 releasably attached to and/or extending proximally from the proximal end 114 of the elongate shaft 110, and fixedly attached to a proximal end of the release wire 120. The securement member 140 may include a proximal portion 142 a distal portion 144, and a lumen 148 (e.g., FIG. 2) extending axially therethrough. The distal portion 144 may include a first clip 146a and a second clip 146b (collectively, 146). While the distal portion 144 is described as including two clips 146, it is contemplated that the distal portion 144 may include fewer than two or greater than two clips 146, as desired.

Figure 3:
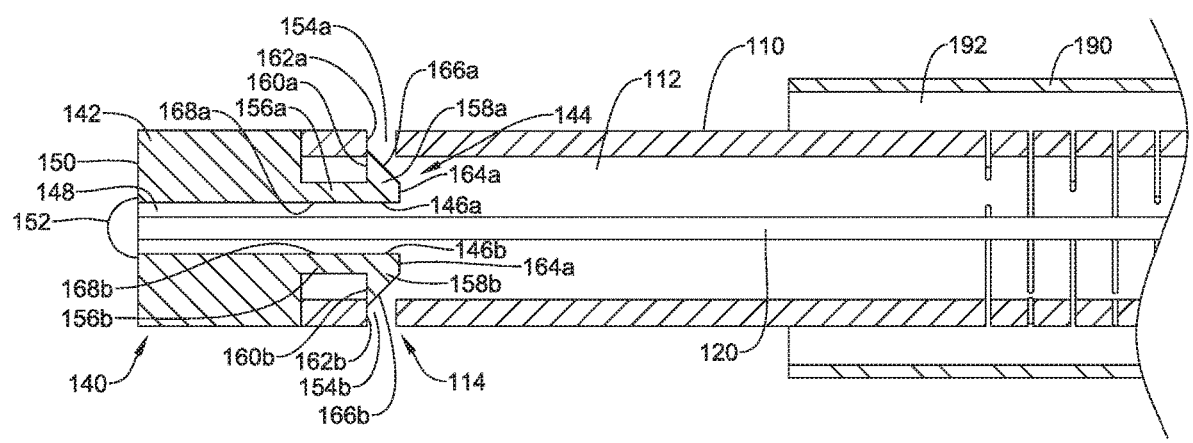
FIG. 3 is a partial cut-away view of a portion of an example medical device system.
Figure 4:
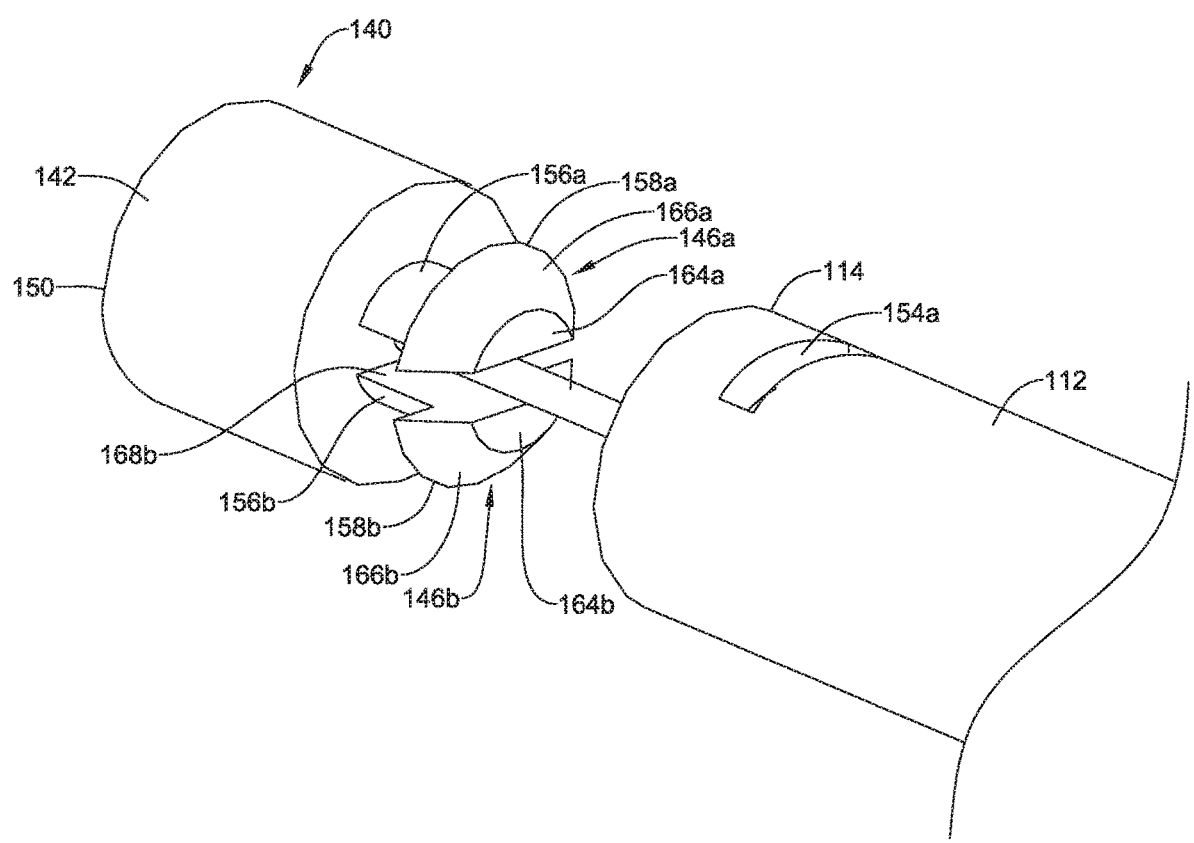
FIG. 4 is a perspective view of a portion of an example medical device system.

FIG. 3 illustrates an enlarged view of the proximal end 114 of the elongate shaft 110 and the securement member 140 with the securement member 140 in a locked configuration with the elongate shaft 110. FIG. 4 illustrates a perspective view of the proximal end 114 of the elongate shaft 110 and the securement member 140 with the securement member 140 in an unlocked configuration with the elongate shaft 110. In some embodiments, the proximal portion 142 of the securement member 140 may be fixedly attached to the distal portion 144 of the securement member 140. In some embodiments, the proximal portion 142 of the securement member 140 may be integrally formed with the distal portion 144 of the securement member 140 as a single unitary structure. The proximal portion 142 of the securement member 140 may take one or more of several different forms, including but not limited to, a generally solid member, a tubular member, or combinations thereof. For example, the proximal portion 142 of the securement member 140 may include an axial lumen 148 extending along a central longitudinal axis of the medical device system 100, the elongate shaft 110, the release wire 120, and/or the securement member 140, the axial lumen 148 being configured to receive a proximal end of the release wire 120. The axial lumen 148 may extend to a proximal end 150 of the securement member 140 where release wire 120 may be fixedly attached to the proximal portion 142 of the securement member 140, for example, using an adhesive, a bonding agent, a weld, or other means of attachment 152. However, the release wire 120 may be secured to the securement member 140 anywhere along a length thereof, as desired.

The clips 146 may be releasably positioned within a first slot 154a and a second slot 154b (collectively, 154) in the elongate shaft 110 adjacent the proximal end 114 thereof. The slots 154 may extend from an inner surface of the elongate shaft 110 to the outer surface of the elongate shaft 110. While the elongate shaft 110 is described as including two slots 154, it is contemplated that the elongate shaft 110 may include fewer than two or greater than two slots 154, as desired. In some cases, the number of slots 154 may be selected to match the number of clips 146, although this is not required. The slots 154 may be uniformly distributed about a circumference of the elongate shaft 110, although this is not required. In one example, the slots 154 may be positioned circumferentially opposite to one another.

When the clips 146 are positioned within, or otherwise engaged with, the slots 154, the securement member 140 is prevented from moving rotationally and/or longitudinally relative to the elongate shaft 110. For example, the slots 154 may be sized and shaped to limit movement of the securement member 140 relative to the elongate shaft 110. For example, each of the slots 154a, 154b, may each extend less than 180° about the circumference of the elongate shaft 110 such that rotation of the securement member 140 is limited by contact between the clips 146 and a sidewall (e.g., in the radial direction) of the slots 154. The length of the slots 154 (in the direction parallel to the longitudinal axis of the elongate shaft 110) may be selected to allow a user to depress or otherwise contact the clips 146 with their fingers or a tool, as will be described in more detail herein. In some examples, the length of the slots 154 and/or the clips 146 may be extended axially along the elongate shaft 110 to provide a larger contact area to depress the clips 146. Proximal movement of the securement member 140 may be limited by contact between the clips 146 and the proximal wall of the slots 154. Distal movement of the securement member 140 may be limited by contact of the proximal portion 242 with the proximal end 114 of the elongate shaft 110. In some embodiments, the securement member 140 may be configured to translate proximally away from the proximal end 114 of the elongate shaft 110 upon application of a proximally directed force to the proximal portion 142 of the securement member 140 with a simultaneously applied radially inward force on the clips 146 while the elongate shaft 110 is maintained in a fixed position, as seen in FIGS. 5 and 6.

Figure 5:
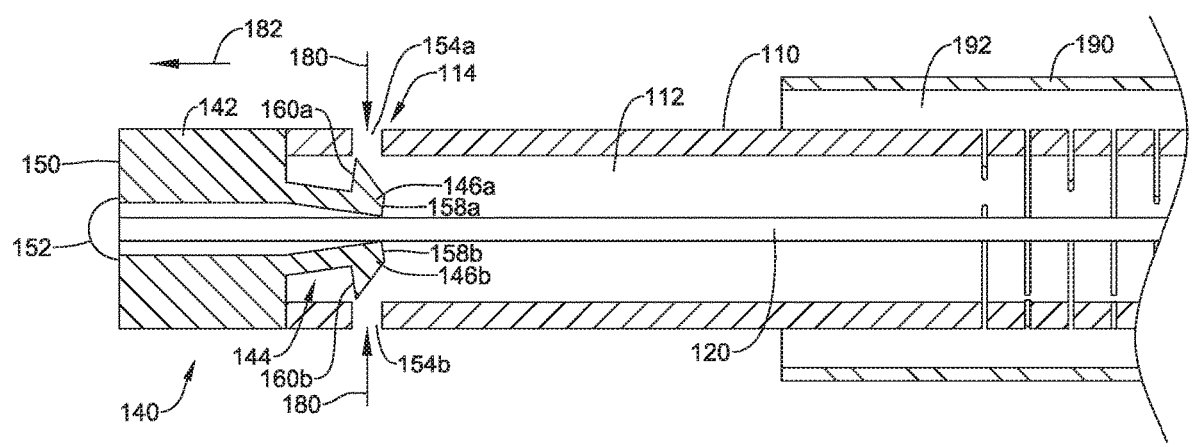
FIGS. 5-6 illustrate actuation of a portion of an example medical device system.
Figure 6:
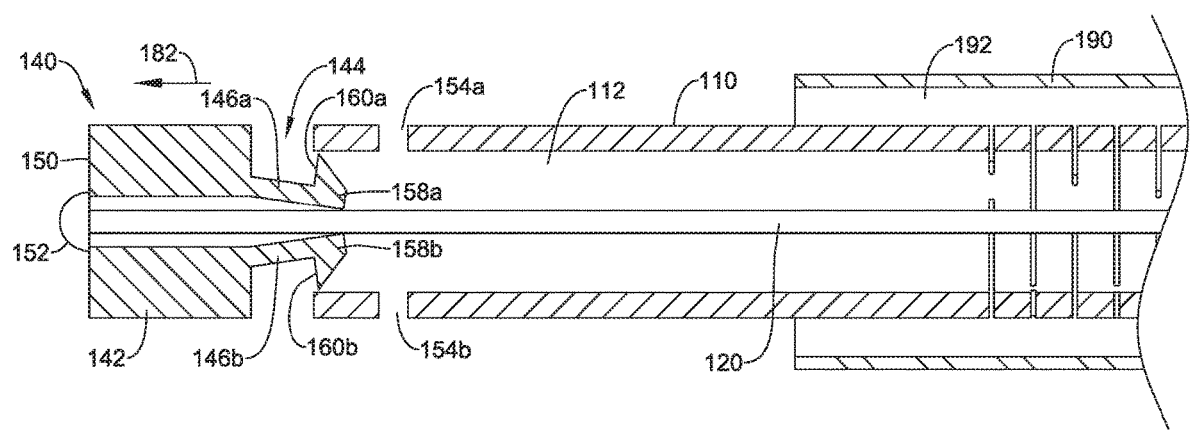

In some embodiments, the clips 146 may be movable between an expanded configuration (e.g., FIGS. 3 and 4) and a compressed configuration (FIGS. 5 and 6). The clips 146 may be biased towards the expanded configuration and assume the compressed configuration under an applied force. In some cases, the clips 146 may be formed from a shape memory material, such as, but not limited to, nitinol. However, the clips 146 may be formed from any material that can be temporarily biased or deformed. Some suitable but non-limiting materials for the clips 146, for example metallic materials, polymer materials, composite materials, etc., are described below.

The clips 146 may each include a proximal arm portion 156a, 156b (collectively, 156) extending from the proximal portion 142 of the securement member 140 towards a distal interlocking portion 158a, 158b (collectively, 158). The distal interlocking portion 158 may be configured to be received within the slots 154 of the elongate shaft 110 to secure the securement member 140 and the release wire 120 relative to the elongate shaft 110. A proximal end 160a, 160b (collectively, 160) of the distal interlocking portion 158 may have an outer diameter or a radial dimension greater than an inner diameter of the elongate shaft 110. Thus, when the distal interlocking portion 158 is positioned within the slots 154, and in an expanded configuration, at least the proximal end 160 may extend radially beyond the inner diameter of the elongate shaft 110. This may cause the proximal end 160 of the clips 146 to engage a proximal edge or surface 162a, 162b (collectively, 162) of the slots 154 if the securement member 140 is actuated in a proximal direction when the distal interlocking portion 158 is engaged with the slots 154. In some embodiments, the distal interlocking portion 158 may reduce in diameter, or taper, from the proximal end 160 towards a distal end 164a, 164b (collectively, 164) thereof. In some cases, an inner surface 168a, 168b (collectively, 168) of the clips 146 may have a recess or groove configured to mate with, grip, or otherwise surround the release wire 120 when the clips 146 are in the compressed configuration, although this is not required. For example, the inner surfaces 168 may each include a hemispherical recess configured to align with and at least partially surround the release wire 120 when the clips 146 are in the compressed configuration.

It is contemplated that the size and/or shape of the proximal arm portion 156 and/or the distal interlocking portion 158 may be adjusted to mitigate premature detachment or excessive force to detach the securement member 140 from the elongate shaft 110. In one example, the clips 146 may be replaced with raised bumps configured to interface with small holes on the elongate shaft 110.

The angled surface 166a, 166b (collectively, 166) may facilitate assembly of the securement member 140 with the elongate shaft 110. For example, the angled surfaces 166 may allow the distal portion 144 of the securement member 140 to be press fit within the lumen 112 of the elongate shaft 110. It is further contemplated that the angled surfaces 166 of the distal interlocking portion 158 may be configured to guide the clips 146 into a compressed configuration for assembly. For example, as described herein, the clips 146 may be configured to be biased towards the expanded (e.g., locked) configuration. During assembly, the clips 146 may be biased by an external force (e.g., the inner diameter of the elongated shaft 110) into a compressed configuration as the distal interlocking portion 158 is distally advanced within the lumen 112. Once the proximal end 160 of the distal interlocking portion 158 is aligned with the slots 154 of the elongate shaft 110, and the biasing force thus removed, the clips 146 return to their expanded configuration. In some embodiments, the proximal portion 142 of the securement member 140 and the proximal end 114 of the elongated shaft 110 may include visual markings to help align the distal interlocking portions 158 with the slots 156, although this is not required.

In some embodiments, the proximal portion 142 of the securement member 140 may be visually distinguishable from the distal portion 144 of the securement member 140 and/or the proximal end 114 of the elongate shaft 110. For example, the proximal portion 142 of the securement member 140 may have and/or include a different coloration from the distal portion 144 of the securement member 140 and/or the elongate shaft 110, a different exterior marking scheme from the distal portion 144 of the securement member 140 and/or the elongate shaft 110, a different exterior texture or surface treatment from the distal portion 144 of the securement member 140 and/or the elongate shaft 110, and/or other and/or additional means of visually distinguishing the proximal portion 142 of the securement member 140 from the distal portion 144 of the securement member 140 and/or the proximal end 114 of the elongate shaft 110. Some suitable but non-limiting materials for the securement member 140, the proximal portion 142, and/or the distal portion 144, for example metallic materials, polymer materials, composite materials, etc., are described below.

The clips 146 of the securement member 140 may define a portion of the lumen 148 wherein the release wire 120 is disposed within the lumen 148 of the securement member 140. The lumen 148 of the securement member 140 may be coaxial with and/or fluidly connected to the lumen 112 of the elongate shaft 110. Proximal axial translation of the proximal portion 142 of the securement member 140 away from and/or relative to the proximal end 114 of the elongate shaft 110 in combination with a radially inward force on the distal interlocking portion 158 may translate the release wire 120 relative to the elongate shaft 110 from the interlocked position to the released position to release the medical device 130 from the distal end 116 of the elongate shaft 110, as will be explained in more detail herein.

Figure 7:
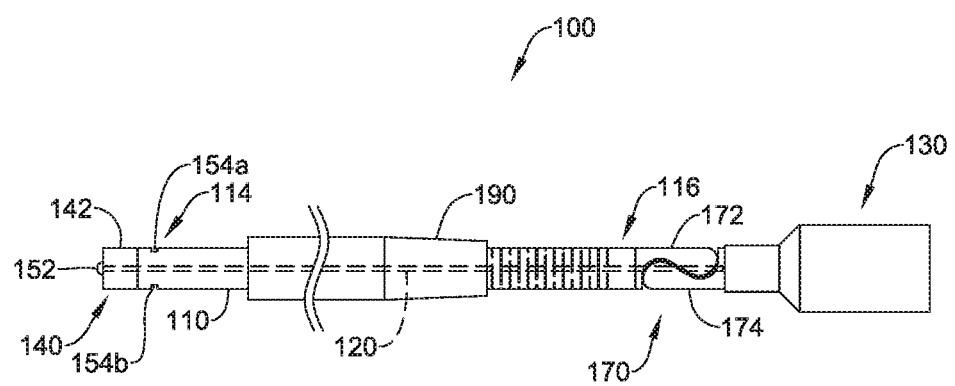
FIGS. 7-8 illustrate actuation of a portion of an example medical device system.

FIGS. 5-8 generally illustrate the medical device 130 being released from the elongate shaft 110, such as at a treatment site, for example. In use, the microcatheter 190 of the medical device system 100 may be inserted into a patient's anatomy and a distal end of the microcatheter 190 may be guided and/or advanced to a location adjacent a treatment site. The medical device 130 disposed at and/or proximate the distal end 116 of the elongate shaft 110 may be inserted into a proximal end of the lumen 192 (e.g., FIG. 2), disposed within the microcatheter 190, and advanced through and/or with the microcatheter 190 to the treatment site. In some embodiments, the medical device 130 may be disposed within the lumen 192 of the microcatheter 190 proximate the distal end of the microcatheter 190. In some embodiments, the medical device 130 may be disposed within the lumen 192 of the microcatheter 190 proximate the distal end of the microcatheter 190 prior to use and/or prior to inserting the microcatheter 190 into the patient's anatomy. Deployment and/or release of the medical device 130 may be performed selectively depending upon the type of medical device and/or the desired treatment process or method. When ready to deploy the medical device 130, the elongate shaft 110 may be advanced and/or translated distally relative to the microcatheter 190 until the medical device 130 is exposed and/or disposed distal of the microcatheter 190, as seen in FIG. 7. Alternatively, the microcatheter 190 may be withdrawn relative to the elongate shaft 110 until the medical device 130 is exposed and/or disposed distal of the microcatheter 190.

A release mechanism 170 may releasably attach the medical device 130 to the distal end 116 of the elongate shaft 110. In some embodiments, the elongate shaft 110 may include a first portion 172 of the release mechanism 170 fixedly attached to the distal end 116 of the elongate shaft 110 and the medical device 130 may include a second portion 174 of the release mechanism 170 fixedly attached to a proximal end of the medical device 130. A distal end of the release wire 120 may slidably engage with the first portion 172 of the release mechanism 170 and the second portion 174 of the release mechanism 170 in the interlocked position, as seen in FIG. 7. The release wire 120 interlocks the first portion 172 of the release mechanism 170 with the second portion 174 of the release mechanism 170 when the distal interlocking portions 158 of the clips 146 of the securement member 140 are disposed within or otherwise engaged with the slots 154 of the elongated shaft 110. When the distal interlocking portions 158 of the clips 146 are biased inwards, as shown at arrows 180 in FIG. 5, the proximal ends 160 of the distal interlocking portions 158 are reduced in profile such that the proximal ends 160 have an outer dimension that is substantially equal to or less than an inner diameter of the elongate shaft 110. This may allow the distal portion 144 of the securement member 140 to slide proximally within the lumen 112 of the elongate shaft 110 under an applied proximal force, shown at arrow 182.

Figure 8:
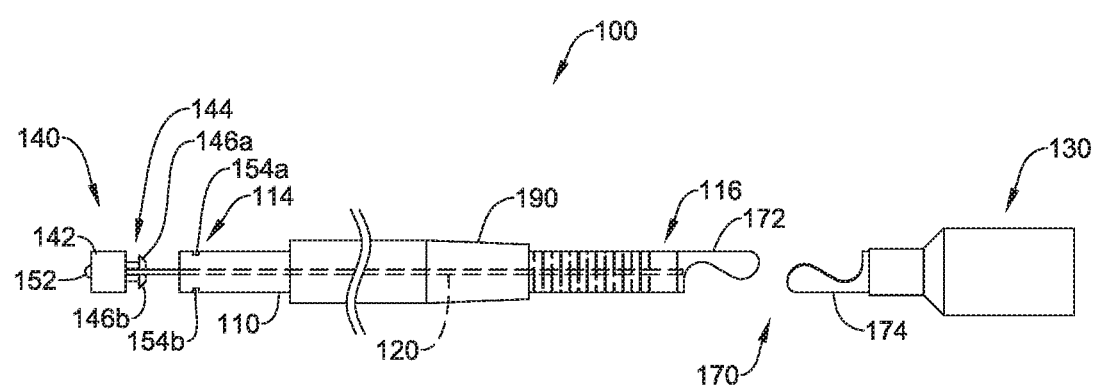
Figure 9:
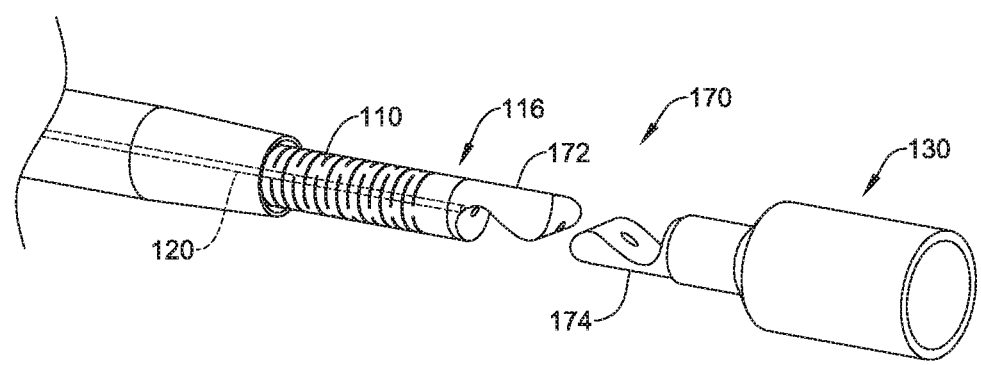
FIG. 9 illustrates an example release mechanism of an example medical device system.

For example, when the proximal portion 142 of the securement member 140 is translated proximally away from the proximal end 114 of the elongate shaft 110 as seen in FIGS. 6 and 8, the release wire 120 is translated in a proximal direction relative to the elongate shaft 110 toward the released position to release the second portion 174 of the release mechanism 170 and/or the medical device 130 from the first portion 172 of the release mechanism 170 and/or the elongate shaft 110, as seen in more detail in FIG. 9. It is contemplated that the release mechanism 170 may remain in an interlocked configuration until the securement member 140 has been proximally actuated by a length equal to or greater than the length of the release mechanism 170. For example, proximal actuation of the securement member 140 by a length less than a length of the release mechanism 170 may not be sufficient to release the medical device 130. In at least some embodiments, the release wire 120 may be slidably disposed within the lumen 112 extending through the elongate shaft 110, a first axial lumen extending through the first portion 172 of the release mechanism 170, and a second axial lumen extending through the second portion 174 of the release mechanism 170. It is contemplated that the release of the medical device 130 may be reversed at any axial location of the securement member 140 between the interlocked configuration and a fully released configuration (FIGS. 8 and 9).

The first axial lumen of the first portion 172 and the second axial lumen of the second portion 174 may be substantially coaxial with the central longitudinal axis and/or the release wire 120 when the medical device 130 is releasably attached to the distal end 116 of the elongate shaft 110. Some suitable but non-limiting materials for the release mechanism 170, the first portion 172, and the second portion 174, for example metallic materials, polymer materials, composite materials, etc., are described below.

Referring back to FIGS. 7 and 8, the elongate shaft 110 may have sufficient length that the proximal end 114 of the elongate shaft 110 and/or the securement member 140 remains proximal of (e.g., extends proximally from) the microcatheter 190 when the medical device 130 is disposed distal of the microcatheter 190. In use, the elongate shaft 110 may have sufficient length to reach from the treatment site to a position outside of the patient where the medical device system 100 may be manipulated by an operator (e.g., clinician, physician, user, etc.). After insertion of the medical device system 100 to the treatment site, the operator of the medical device system 100 may place a first hand on the proximal end 114 of the elongate shaft 110 and a second hand on the proximal portion 142 of the securement member 140 in order to manipulate the proximal portion 142 and/or the distal portion 144 of the securement member 140 and/or the release wire 120 to release the medical device 130. For example, the operator may grip the proximal portion of 142 of the securement member 140 with a portion of the second hand (e.g., palm and/or fingers) and use two or more fingers of the second hand to depress the distal interlocking portions 158 of the clips 146. The distal portion 144 of the securement member 140 may be disposed proximal of a proximal end of the microcatheter 190 when the medical device 130 is disposed distal of the microcatheter 190 to allow for access to the distal interlocking portions 158 and/or the slots 156.

In at least some embodiments, the distal portion 144 of the securement member 140 may undergo elastic deformation during compression of the clips 146 and/or proximal translation of the proximal portion 142 of the securement member 140 relative to the elongate shaft 110. Upon removal of the biasing force on the clips 146 (e.g., the operator's applied force or the force of the inner diameter of the elongated shaft 110), the clips 146 may return to their expanded configuration without application of an external force (e.g., FIGS. 6 and 8).

While not explicitly shown, the medical device system 100 may include an introducer configured to load the medical device 130 into the microcatheter 190. The introducer may be a tubular member having a lumen extending from a proximal end to a distal end. The introducer may hold the medical device 130 to a reduced diameter and/or in a delivery configuration for loading into the microcatheter 190. After loading the medical device 130 into the microcatheter 190, the introducer may be proximally withdrawn over and relative to the elongate shaft 110 and the securement member 140 and removed from the medical device system 100.

In use, a method of delivering the medical device 130 to a treatment site (e.g., a vein, an artery, etc.) may include inserting the microcatheter 190 into a patient's anatomy and guiding the distal end of the microcatheter 190 to a location adjacent the treatment site. The method may include inserting the medical device 130 disposed at and/or proximate the distal end 116 of the elongate shaft 110 into a proximal end of the lumen 192 disposed within the microcatheter 190. In some embodiments, the medical device 130 may be inserted into the lumen 192 of the microcatheter 190 after the microcatheter 190 is inserted into the patient's anatomy. The method may include advancing the medical device 130 through the microcatheter 190 to the treatment site. The medical device 130 may be releasably attached to the distal end 116 of the elongate shaft 110 by a pull wire (e.g., the release wire 120, etc.) extending through the lumen 112 within the elongate shaft 110. The securement member 140 may extend proximally from the elongate shaft 110, and the securement member 140 may be releasably coupled to the elongate shaft 110 and fixedly coupled to the pull wire (e.g., the release wire 120, etc.), as described herein. Alternatively, in some embodiments, the medical device 130 may be inserted into the proximal end of the lumen 192 of the microcatheter 190 and advanced through the microcatheter 190 to a distal end of the microcatheter 190 before the microcatheter 190 is inserted into the patient's anatomy.

As discussed herein, the proximal portion 142 of the securement member 140 may be fixedly attached to a proximal end of the pull wire (e.g., the release wire 120, etc.) and the distal portion 144 of the securement member 140 may be releasably coupled to the proximal end 114 of the elongate shaft 110. The first portion 172 of the release mechanism 170 may be attached to the distal end 116 of the elongate shaft 110, and the second portion 174 of the release mechanism 170 may be fixedly attached to a proximal end of the medical device 130. The pull wire (e.g., the release wire 120, etc.) may be slidably disposed within the lumen 112 of the elongate shaft 110, the first axial lumen of the first portion 172 of the release mechanism 170, and the second axial lumen of the second portion 174 of the release mechanism 170.

The method may include compressing the distal interlocking portion 158 of the distal portion 144 of the securement member 140 while applying a proximal force to the proximal portion of the securement member 140 to uncouple the distal portion 144 of the securement member 140 from the elongate shaft 110. The method may further include translating the proximal portion 142 of the securement member 140 proximally away from the proximal end 114 of the elongate shaft 110 while the elongate shaft 110 is maintained in a fixed position with respect to the treatment site to translate the pull wire (e.g., the release wire 120, etc.) relative to the elongate shaft 110 and/or the release mechanism 170 to shift the pull wire (e.g., the release wire 120, etc.) from an interlocked position to a released position, thereby releasing the medical device 130 from the elongate shaft 110.

The method may also include proximal withdrawal of the elongate shaft 110 and/or the microcatheter 190 from the treatment site. For example, in some embodiments, the elongate shaft 110 may be withdrawn proximally through the lumen 192 of the microcatheter 190 and removed, and the microcatheter 190 may then be withdrawn and/or removed from the patient's anatomy. In some embodiments, the elongate shaft 110 may be withdrawn proximally far enough for the distal end 116 of the elongate shaft 110 and/or the first portion 172 of the release mechanism 170 to be positioned within the distal end and/or the lumen 192 of the microcatheter 190. The elongate shaft 110 and the microcatheter 190 may then be withdrawn together from the patient's anatomy.

In some embodiments, the elongate shaft 110 may be removed through the lumen 192 of the microcatheter 190, and the microcatheter 190 may be left and/or held in place within the patient's anatomy. If needed, a second elongate shaft and associated second medical device may then be inserted into the proximal end of the lumen 192 of the microcatheter 190 and advanced to the treatment site for deployment. Additional repetitions of the device(s) described herein, as well as the described method steps, may be used as needed or desired for a particular procedure.

Figure 10:
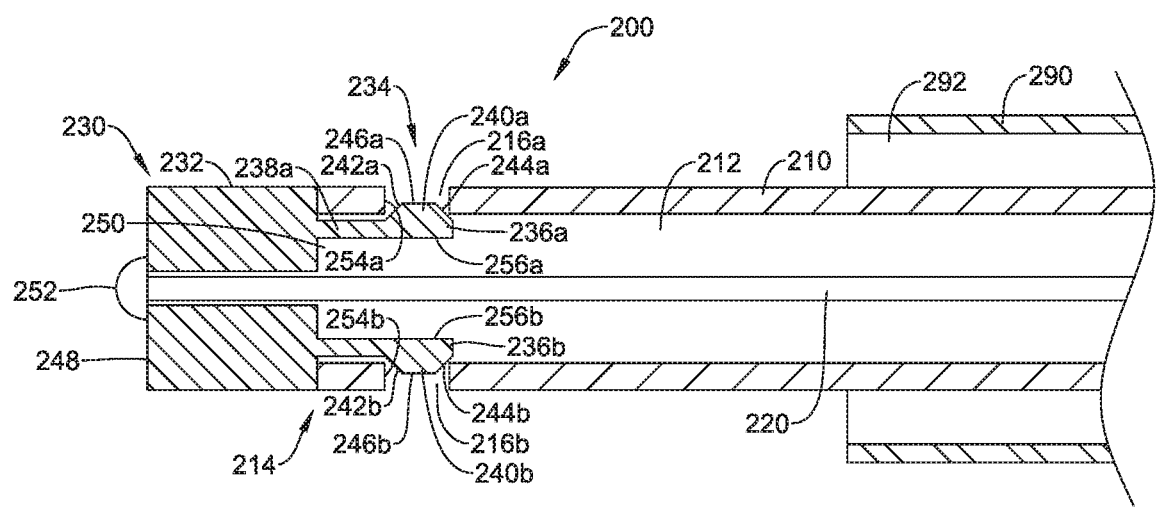
FIG. 10 illustrates a partial cut-away view of another example medical device system.

FIG. 10 illustrate aspects of another example medical device system 200. The medical device system 200 may include an elongate shaft 210 having a lumen 212 extending from a proximal end 214 of the elongate shaft 210 to a distal end of the elongate shaft 210. The elongate shaft 210 may be similar in form and function to the elongate shaft 110 described herein. In some embodiments, the elongate shaft 210 may be a catheter, a hypotube, or other similar tubular structure. In some embodiments, at least a portion of the elongate shaft 210 may include micromachining, a plurality of cuts or weakened areas, some degree of material removal, etc. to provide increased flexibility along a length of the elongate shaft 210 for navigating tortuous vasculature. Some suitable but non-limiting materials for the elongate shaft 210, for example metallic materials, polymer materials, composite materials, etc., are described below.

The medical device system 200 may include a release wire 220 slidably disposed within the lumen 212 of the elongate shaft 210. A medical device (not explicitly shown) may be disposed proximate the distal end of the elongate shaft 210. The release wire 220 may be axially slidable between an interlocked position and a released position. The release wire 220 may be configured to releasably attach the medical device to the distal end of the elongate shaft 210. The medical device may be configured to expand from a delivery configuration to a deployed configuration. The medical device may be a vascular occlusion device, but other suitable medical devices transported, delivered, used, released, etc. in a similar manner are also contemplated, including but not limited to, embolic coils, stents, embolic filters, replacement heart valves, other occlusion devices, and/or other medical implants, etc. In some embodiments, the release wire 220 may be alternately and/or interchangeably referred to as a pull wire, an actuation wire, and/or a locking wire. The release wire 220 may generally be a solid wire or shaft, but may also be tubular in some embodiments. Some suitable but non-limiting materials for the release wire 220, for example metallic materials, polymer materials, composite materials, etc., are described below.

In some embodiments, the medical device system 200 may include a microcatheter 290 sized and configured to deliver the medical device to a treatment site in a delivery configuration. The elongate shaft 210 and the medical device 130 may be slidably disposed within a lumen 292 of the microcatheter 290. In some embodiments, the microcatheter 290 may facilitate percutaneous delivery of the medical device to the treatment site. Some suitable but non-limiting materials for the microcatheter 290, for example metallic materials, polymer materials, composite materials, etc., are described below.

As seen in FIG. 10, the medical device system 200 may include a securement member 230 releasably attached to and/or extending proximally from the proximal end 214 of the elongate shaft 210, and fixedly attached to a proximal end of the release wire 220. The securement member 230 may include a proximal portion 232 a distal portion 234, and a lumen 250 extending axially therethrough. The distal portion 234 may include a first clip 236a and a second clip 236b (collectively, 236). While the distal portion 234 is described as including two clips 236, it is contemplated that the distal portion 234 may include fewer than two or greater than two clips 236, as desired.

FIG. 10 illustrates the securement member 230 in a locked configuration with the elongate shaft 210. In some embodiments, the proximal portion 232 of the securement member 230 may be fixedly attached to the distal portion 234 of the securement member 230. In some embodiments, the proximal portion 232 of the securement member 230 may be integrally formed with the distal portion 234 of the securement member 230 as a single unitary structure. The proximal portion 232 of the securement member 230 may take one or more of several different forms, including but not limited to, a generally solid member, a tubular member, or combinations thereof. For example, the proximal portion 232 of the securement member 230 may include an axial lumen 250 extending along a central longitudinal axis of the medical device system 200, the elongate shaft 210, the release wire 220, and/or the securement member 230, the axial lumen 250 being configured to receive a proximal end of the release wire 220. The axial lumen 250 may extend to a proximal end 248 of the securement member 230 where the release wire 220 may be fixedly attached to the proximal portion 232 of the securement member 230, for example, using an adhesive, a bonding agent, a weld, or other means of attachment 252. However, the release wire 220 may be secured to the securement member 230 anywhere along a length thereof, as desired.

The clips 236 may be releasably positioned within one or more slots 216a, 216b (collectively, 216) in the elongate shaft 210 adjacent the proximal end 214 thereof. While the elongate shaft 210 is described as including two slots 216, it is contemplated that the elongate shaft 210 may include fewer than two or greater than two slots 216, as desired. In some cases, the number of slots 216 may be selected to match the number of clips 236, although this is not required. When the clips 236 are positioned within, or otherwise engaged with, the slots 216, the securement member 230 is prevented from moving rotationally and/or longitudinally relative to the elongate shaft 210. For example, the slots 216 may be sized and shaped to limit movement of the securement member 230 relative to the elongate shaft 210. For example, each of the slots 216a, 216b, may each extend less than 180° about the circumference of the elongate shaft 210 such that rotation of the securement member 230 is limited by contact between the clips 236 and a sidewall (e.g., in the radial direction) of the slots 216. The length of the slots 216 (in the direction parallel to the longitudinal axis of the elongate shaft 210) may be selected to allow a user to depress or otherwise contact the clips 236 with their fingers or a tool, although this is not required. In some examples, the length of the slots 216 and/or the clips 236 may be extended axially along the elongate shaft 210 to provide a larger contact area to depress the clips 236. Proximal movement of the securement member 230 may be limited by contact between the clips 236 and the proximal wall 254a, 254b (collectively, 254) of the slots 216. Distal movement of the securement member 230 may be limited by contact of the proximal portion 232 with the proximal end 214 of the elongate shaft 210. In some embodiments, the securement member 230 may be configured to translate proximally away from the proximal end 214 of the elongate shaft 210 upon application of a proximally directed force to the proximal portion 232 of the securement member 230.

In some embodiments, the clips 236 may be movable between an expanded configuration and a compressed configuration (not explicitly shown). The clips 236 may be biased towards the expanded configuration and assume the compressed configuration under an applied force. In some cases, the clips 236 may be formed from a shape memory material, such as, but not limited to, nitinol. However, the clips 236 may be formed from any material that can be temporarily biased or deformed. Some suitable but non-limiting materials for the clips 236, for example metallic materials, polymer materials, composite materials, etc., are described below.

The clips 236 may each include a proximal arm portion 238a, 238b (collectively, 238) extending from the proximal portion 232 of the securement member 230 towards a distal interlocking portion 240a, 240b (collectively, 240). The distal interlocking portion 240 may be configured to be received within the slots 216 of the elongate shaft 210 to secure the securement member 230 and the release wire 220 relative to the elongate shaft 210. A proximal end region 242a, 242b (collectively, 242) of the distal interlocking portion 240 may have an angled surface which increases in outer diameter (or outer profile) from the proximal end thereof towards an intermediate region 246a, 246b (collectively 246) of the distal interlocking portion 240. The intermediate region 246 may have an outer diameter or an outer dimension greater than an inner diameter of the elongate shaft 210. Thus, when the distal interlocking portion 240 is positioned within the slots 216, and in an expanded configuration, at least the intermediate region 246 may extend radially beyond the inner diameter of the elongate shaft 210. This may cause at least a portion of the proximal end region 242 of the clips 236 to engage a proximal edge or surface 254a, 254b (collectively, 254) of the slots 216 if the securement member 230 is actuated in a proximal direction when the distal interlocking portion 240 is engaged with the slots 216. In some embodiments, the distal interlocking portion 240 may reduce in diameter, or taper, from the intermediate region 246 towards a distal end defining an angled distal end region 244a, 244b (collectively, 244) thereof. In some embodiments, the intermediate region 246 may be a region having a generally uniform outer diameter. In other embodiments, the intermediate region 246 may be the intersection of the proximal end region 242 and the distal end region 244.

In some cases, an inner surface 256a, 256b (collectively, 256) of the clips 236 may have a recess or groove configured to mate with, grip, or otherwise surround the release wire 220 when the clips 236 are in the compressed configuration, although this is not required. For example, the inner surfaces 256 may each include a hemispherical recess configured to align with and at least partially surround the release wire 220 when the clips 236 are in the compressed configuration.

The distal end region 244 of the distal interlocking portion 240 may facilitate assembly of the securement member 230 with the elongate shaft 210. For example, the angled surfaces 244 may allow the distal portion 234 of the securement member 230 to be press fit within the lumen 212 of the elongate shaft 210. It is further contemplated that the angled surfaces 244 of the distal interlocking portion 240 may be configured to guide the clips 236 into a compressed configuration for assembly. For example, as described herein, the clips 236 may be configured to be biased towards the expanded (e.g., locked) configuration. During assembly, the clips 236 may be biased by an external force (e.g., the inner diameter of the elongated shaft 210) into a compressed configuration as the distal interlocking portion 240 is distally advanced within the lumen 212. Once the proximal end region 242 and/or intermediate region 246 of the distal interlocking portion 240 is aligned with the slots 216 of the elongate shaft 210, and the biasing force thus removed, the clips 236 return to their expanded configuration. In some embodiments, the proximal portion 232 of the securement member 230 and the proximal end 214 of the elongated shaft 210 may include visual markings to help align the distal interlocking portions 240 with the slots 238, although this is not required.

In some embodiments, the proximal portion 232 of the securement member 230 may be visually distinguishable from the distal portion 234 of the securement member 230 and/or the proximal end 214 of the elongate shaft 210. For example, the proximal portion 232 of the securement member 230 may have and/or include a different coloration from the distal portion 234 of the securement member 230 and/or the elongate shaft 210, a different exterior marking scheme from the distal portion 234 of the securement member 230 and/or the elongate shaft 210, a different exterior texture or surface treatment from the distal portion 234 of the securement member 230 and/or the elongate shaft 210, and/or other and/or additional means of visually distinguishing the proximal portion 232 of the securement member 230 from the distal portion 234 of the securement member 230 and/or the proximal end 214 of the elongate shaft 210. Some suitable but non-limiting materials for the securement member 230, the proximal portion 232, and/or the distal portion 234, for example metallic materials, polymer materials, composite materials, etc., are described below.

The proximal end region 242 of the distal interlocking portion 240 may facilitate detachment of the securement member 230 from the elongate shaft 210 without the need for an applied external radial force on the distal interlocking portion 240. For example, as a proximal force is applied to the securement member 230, the angled surfaces 242 may cause the elongate shaft to exert a force on the distal interlocking region 240 which causes the intermediate region 246 and/or distal end regions 244 to be biased inwards or compressed such that the intermediate region 246 has as outer dimension substantially equal to or less than the inner diameter of the elongate shaft 210. For example, the proximal end region 242 may form a press fit with the lumen 212 of the elongate shaft 210. This may allow the distal portion 234 of the securement member 230 to slide proximally within the lumen 212 of the elongate shaft 210 under an applied proximal force. It is contemplated that the angle and/or length of the proximal end regions 242 may be selected such that the securement member 230 is not inadvertently actuated but does not require an excessive amount of force to actuate the securement member 230.

The clips 236 of the securement member 230 may define a portion of the lumen 250 wherein the release wire 220 is disposed within the lumen 250 of the securement member 230. The lumen 250 of the securement member 230 may be coaxial with and/or fluidly connected to the lumen 212 of the elongate shaft 210. Proximal axial translation of the proximal portion 232 of the securement member 230 away from and/or relative to the proximal end 214 of the elongate shaft 210 in combination with a radially inward force on the distal interlocking portion 240 may translate the release wire 220 relative to the elongate shaft 210 from the interlocked position to the released position to release the medical device from the distal end of the elongate shaft 210, as will be explained in more detail herein.

The medical device may be released from the elongate shaft 210 in a manner similar to the medical device 130 described herein. In use, the microcatheter 290 of the medical device system 200 may be inserted into a patient's anatomy and a distal end of the microcatheter 290 may be guided and/or advanced to a location adjacent a treatment site. The medical device disposed at and/or proximate the distal end of the elongate shaft 210 may be inserted into a proximal end of the lumen 292, disposed within the microcatheter 290, and advanced through and/or with the microcatheter 290 to the treatment site. In some embodiments, the medical device may be disposed within the lumen 292 of the microcatheter 290 proximate the distal end of the microcatheter 290. In some embodiments, the medical device may be disposed within the lumen 292 of the microcatheter 290 proximate the distal end of the microcatheter 290 prior to use and/or prior to inserting the microcatheter 290 into the patient's anatomy. Deployment and/or release of the medical device may be performed selectively depending upon the type of medical device and/or the desired treatment process or method. When ready to deploy the medical device, the elongate shaft 210 may be advanced and/or translated distally relative to the microcatheter 290 until the medical device is exposed and/or disposed distal of the microcatheter 290. Alternatively, the microcatheter 290 may be withdrawn relative to the elongate shaft 210 until the medical device is exposed and/or disposed distal of the microcatheter 290.

A release mechanism (not explicitly shown) may releasably attach the medical device to the distal end of the elongate shaft 210. The release mechanism may be similar in form and function to the release mechanism 170 described herein. In some embodiments, the elongate shaft 210 may include a first portion of the release mechanism fixedly attached to the distal end of the elongate shaft 210 and the medical device may include a second portion of the release mechanism fixedly attached to a proximal end of the medical device. A distal end of the release wire 220 may slidably engage with the first portion of the release mechanism and the second portion of the release mechanism in the interlocked position. The release wire 220 interlocks the first portion of the release mechanism with the second portion of the release mechanism when the distal interlocking portions 240 of the clips 236 of the securement member 230 are disposed within or otherwise engaged with the slots 216 of the elongated shaft 210. When the distal interlocking portions 240 of the clips 236 are biased inwards via proximal retraction of the securement member 230 (and/or through an applied radially inward force), the proximal end regions 242 and the intermediate regions 246 of the distal interlocking portions 240 are reduced in profile such that the proximal end regions 242 and/or the intermediate regions 246 have an outer dimension that is substantially equal to or less than an inner diameter of the elongate shaft 210. This may allow the distal portion 234 of the securement member 230 to slide proximally within the lumen 212 of the elongate shaft 210 under an applied proximal force.

For example, when the proximal portion 232 of the securement member 230 is translated proximally away from the proximal end 214 of the elongate shaft 210, the release wire 220 is translated in a proximal direction relative to the elongate shaft 210 toward the released position to release the second portion of the release mechanism and/or the medical device from the first portion of the release mechanism and/or the elongate shaft 210. It is contemplated that the release mechanism may remain in an interlocked configuration until the securement member 230 has been proximally actuated by a length equal to or greater than the length of the release mechanism. For example, proximal actuation of the securement member 230 by a length less than a length of the release mechanism may not be sufficient to release the medical device. In at least some embodiments, the release wire 220 may be slidably disposed within the lumen 212 extending through the elongate shaft 210, a first axial lumen extending through the first portion of the release mechanism, and a second axial lumen extending through the second portion of the release mechanism. It is contemplated that the release of the medical device may be reversed at any axial location of the securement member 230 between the interlocked configuration and a fully released configuration.

The elongate shaft 210 may have sufficient length that the proximal end 214 of the elongate shaft 210 and/or the securement member 230 remains proximal of (e.g., extends proximally from) the microcatheter 290 when the medical device is disposed distal of the microcatheter 290. In use, the elongate shaft 210 may have sufficient length to reach from the treatment site to a position outside of the patient where the medical device system 200 may be manipulated by an operator (e.g., clinician, physician, user, etc.). After insertion of the medical device system 200 to the treatment site, the operator of the medical device system 200 may place a first hand on the proximal end 214 of the elongate shaft 210 and a second hand on the proximal portion 232 of the securement member 230 in order to manipulate the proximal portion 232 and/or the distal portion 234 of the securement member 230 and/or the release wire 220 to release the medical device 130. In a first example, the operator may actuate the securement member 230 with only a proximal force on the proximal portion 232 of the securement member 230. In another example, the operator may grip the proximal portion of 232 of the securement member 230 with a portion of the second hand (e.g., palm and/or fingers) and use two or more fingers of the second hand to depress the distal interlocking portions 240 of the clips 236. The distal portion 234 of the securement member 230 may be disposed proximal of a proximal end of the microcatheter 290 when the medical device is disposed distal of the microcatheter 290 to allow for access to the distal interlocking portions 240 and/or the slots 238.

In at least some embodiments, the distal portion 234 of the securement member 230 may undergo elastic deformation during compression of the clips 236 and/or proximal translation of the proximal portion 232 of the securement member 230 relative to the elongate shaft 210. Upon removal of the biasing force on the clips 236 (e.g., the operator's applied force or the force of the inner diameter of the elongated shaft 210), the clips 236 may return to their expanded configuration without application of an external force.

While not explicitly shown, the medical device system 200 may include an introducer configured to load the medical device into the microcatheter 290. The introducer may be a tubular member having a lumen extending from a proximal end to a distal end. The introducer may hold the medical device to a reduced diameter and/or in a delivery configuration for loading into the microcatheter 290. After loading the medical device into the microcatheter 290, the introducer may be proximally withdrawn over and relative to the elongate shaft 210 and the securement member 230 and removed from the medical device system 200.

In use, a method of delivering the medical device (not explicitly shown) to a treatment site (e.g., a vein, an artery, etc.) may include inserting the microcatheter 290 into a patient's anatomy and guiding the distal end of the microcatheter 290 to a location adjacent the treatment site. The method may include inserting the medical device disposed at and/or proximate the distal end of the elongate shaft 210 into a proximal end of the lumen 292 disposed within the microcatheter 290. In some embodiments, the medical device may be inserted into the lumen 292 of the microcatheter 290 after the microcatheter 290 is inserted into the patient's anatomy. The method may include advancing the medical device through the microcatheter 290 to the treatment site. The medical device may be releasably attached to the distal end of the elongate shaft 210 by a pull wire (e.g., the release wire 220, etc.) extending through the lumen 212 within the elongate shaft 210. The securement member 230 may extend proximally from the elongate shaft 210, and the securement member 230 may be releasably coupled to the elongate shaft 210 and fixedly coupled to the pull wire (e.g., the release wire 220, etc.), as described herein. Alternatively, in some embodiments, the medical device may be inserted into the proximal end of the lumen 292 of the microcatheter 290 and advanced through the microcatheter 290 to a distal end of the microcatheter 290 before the microcatheter 290 is inserted into the patient's anatomy.

As discussed herein, the proximal portion 232 of the securement member 230 may be fixedly attached to a proximal end of the pull wire (e.g., the release wire 220, etc.) and the distal portion 234 of the securement member 230 may be releasably coupled to the proximal end 214 of the elongate shaft 210. The first portion of the release mechanism may be attached to the distal end of the elongate shaft 210, and the second portion of the release mechanism may be fixedly attached to a proximal end of the medical device. The pull wire (e.g., the release wire 220, etc.) may be slidably disposed within the lumen 212 of the elongate shaft 210, the first axial lumen of the first portion of the release mechanism, and the second axial lumen of the second portion of the release mechanism.

The method may include applying a proximal force to the proximal portion 232 of the securement member 230 to uncouple the distal portion 234 of the securement member 230 from the elongate shaft 210. In some instances, the method may include compressing the distal interlocking portion 240 of the distal portion 234 of the securement member 230 while applying a proximal force to the proximal portion 232 of the securement member 230, although this is not required. The method may further include translating the proximal portion 232 of the securement member 230 proximally away from the proximal end 214 of the elongate shaft 210 while the elongate shaft 210 is maintained in a fixed position with respect to the treatment site to translate the pull wire (e.g., the release wire 220, etc.) relative to the elongate shaft 210 and/or the release mechanism to shift the pull wire (e.g., the release wire 220, etc.) from an interlocked position to a released position, thereby releasing the medical device from the elongate shaft 210.

The method may also include proximal withdrawal of the elongate shaft 210 and/or the microcatheter 290 from the treatment site. For example, in some embodiments, the elongate shaft 210 may be withdrawn proximally through the lumen 292 of the microcatheter 290 and removed, and the microcatheter 290 may then be withdrawn and/or removed from the patient's anatomy. In some embodiments, the elongate shaft 210 may be withdrawn proximally far enough for the distal end of the elongate shaft 210 and/or the first portion of the release mechanism to be positioned within the distal end and/or the lumen 292 of the microcatheter 290. The elongate shaft 210 and the microcatheter 290 may then be withdrawn together from the patient's anatomy.

In some embodiments, the elongate shaft 210 may be removed through the lumen 292 of the microcatheter 290, and the microcatheter 290 may be left and/or held in place within the patient's anatomy. If needed, a second elongate shaft and associated second medical device may then be inserted into the proximal end of the lumen 292 of the microcatheter 290 and advanced to the treatment site for deployment. Additional repetitions of the device(s) described herein, as well as the described method steps, may be used as needed or desired for a particular procedure.

The materials that can be used for the various components of the medical device system 100, 200 the elongate shaft 110, 210, the release wire 120, 220, the medical device 130, the securement member 140, 230, the release mechanism 170, the introducer, and/or the microcatheter 190, 290, etc. (and/or other systems disclosed herein) and the various elements thereof disclosed herein may include those commonly associated with medical devices. For simplicity purposes, the following discussion makes reference to the medical device system 100, 200 the elongate shaft 110, 210, the release wire 120, 220, the medical device 130, the securement member 140, 230, the release mechanism 170, the introducer, and/or the microcatheter 190, 290, etc. However, this is not intended to limit the devices and methods described herein, as the discussion may be applied to other elements, members, components, or devices disclosed herein, such as, but not limited to, the medical device system 100, 200 the elongate shaft 110, 210, the release wire 120, 220, the medical device 130, the securement member 140, 230, the release mechanism 170, the introducer, and/or the microcatheter 190, 290, etc. and/or elements or components thereof.

In some embodiments, the medical device system 100, 200 the elongate shaft 110, 210, the release wire 120, 220, the medical device 130, the securement member 140, 230, the release mechanism 170, the introducer, and/or the microcatheter 190, 290, etc., and/or components thereof (such as, but not limited to, the proximal portion 142, 232, the distal portion 144, 244, the first portion 172, the second portion 174, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. For example, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical device system 100, 200 the elongate shaft 110, 210, the release wire 120, 220, the medical device 130, the securement member 140, 230, the release mechanism 170, the introducer, and/or the microcatheter 190, 290, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the medical device system 100, 200 the elongate shaft 110, 210, the release wire 120, 220, the medical device 130, the securement member 140, 230, the release mechanism 170, the introducer, and/or the microcatheter 190, 290, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 100, 200 the elongate shaft 110, 210, the release wire 120, 220, the medical device 130, the securement member 140, 230, the release mechanism 170, the introducer, and/or the microcatheter 190, 290, etc. to achieve the same result.

In some embodiments, a degree of Magnetic Resonance Imaging (MRI) compatibility is imparted into the medical device system 100, 200 the elongate shaft 110, 210, the release wire 120, 220, the medical device 130, the securement member 140, 230, the release mechanism 170, the introducer, and/or the microcatheter 190, 290, etc. For example, the medical device system 100, 200 the elongate shaft 110, 210, the release wire 120, 220, the medical device 130, the securement member 140, 230, the release mechanism 170, the introducer, and/or the microcatheter 190, 290, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The medical device system 100, 200 the elongate shaft 110, 210, the release wire 120, 220, the medical device 130, the securement member 140, 230, the release mechanism 170, the introducer, and/or the microcatheter 190, 290, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the medical device system 100, 200 the elongate shaft 110, 210, the release wire 120, 220, the medical device 130, the securement member 140, 230, the release mechanism 170, the introducer, and/or the microcatheter 190, 290, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the medical device system 100, 200 the elongate shaft 110, 210, the release wire 120, 220, the medical device 130, the securement member 140, 230, the release mechanism 170, the introducer, and/or the microcatheter 190, 290, etc. disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical device system 100, 200 the elongate shaft 110, 210, the release wire 120, 220, the medical device 130, the securement member 140, 230, the release mechanism 170, the introducer, and/or the microcatheter 190, 290, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical device system 100, 200 the elongate shaft 110, 210, the release wire 120, 220, the medical device 130, the securement member 140, 230, the release mechanism 170, the introducer, and/or the microcatheter 190, 290, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine);

antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed:

1. A medical device system, comprising:
   an elongate shaft having a lumen extending from a proximal end of the elongate shaft to a distal end of the elongate shaft;
   at least one slot extending from an inner surface to an outer surface of the elongate shaft adjacent to the proximal end of the elongate shaft;
   a release wire disposed within the lumen of the elongate shaft, wherein the release wire is configured to releasably attach a medical device to the distal end of the elongate shaft; and
   a securement member having a proximal portion and a distal portion, the proximal portion fixedly secured to a proximal end of the release wire and the distal portion having at least one clip movable between an expanded configuration and a compressed configuration and releasably coupled within the at least one slot of the elongate shaft;
   wherein the securement member is configured to translate proximally away from the proximal end of the elongate shaft upon application of a proximally-directed force to the proximal portion of the securement member and upon movement of the at least one clip to the compressed configuration while the elongate shaft is maintained in a fixed position.

2. The medical device system of claim 1, wherein the movement of the at least one clip to the compressed configuration is an application of a radially inward directed force to the at least one clip.

3. The medical device system of claim 2, wherein the radially inward directed force to the at least one clip is applied by an operator.

4. The medical device system of claim 2, wherein the radially inward directed force to the at least one clip is applied by the inner surface of the elongate shaft.

5. The medical device system of claim 1, wherein the at least one clip includes a proximal portion and a distal interlocking portion.

6. The medical device system of claim 5, wherein the distal interlocking portion of the at least one clip is configured to be positioned within the at least one slot.

7. The medical device system of claim 6, wherein when in the expanded configuration at least a portion of the distal interlocking portion of the at least one clip has a radial extent greater than a radial extent of an inner diameter of the elongate shaft.

8. The medical device system of claim 5, wherein when in the compressed configuration, the distal interlocking portion of the at least one clip has a radial extent dimension substantially equal to or less than a radial extent of an inner diameter of the elongate shaft.

9. The medical device system of claim 5, wherein the distal interlocking portion of the at least one clip includes a distally tapering surface.

10. The medical device system of claim 5, wherein the distal interlocking portion of the at least one clip include a proximally tapering surface.

11. A medical device system, comprising:
    an elongate shaft having a lumen extending from a proximal end of the elongate shaft to a distal end of the elongate shaft;
    a first slot and a second slot positioned circumferentially opposite from the first slot, the first and second slots each extending from an inner surface to an outer surface of the elongate shaft adjacent to the proximal end of the elongate shaft;
    a release wire disposed within the lumen of the elongate shaft, wherein the release wire is configured to releasably attach a medical device to the distal end of the elongate shaft; and
    a securement member, the securement member comprising:
    a proximal portion fixedly secured to a proximal end of the release wire;
    a first clip extending distally from the proximal portion and releasably coupled with the first slot; and
    a second clip extending distally from the proximal portion and releasably coupled with the second slot;
    wherein the first and second clips are movable between an expanded configuration and a compressed configuration;
    wherein the securement member is configured to translate proximally away from the proximal end of the elongate shaft upon application of a proximally-directed force to the proximal portion of the securement member and upon movement of the first and second clips to the compressed configuration while the elongate shaft is maintained in a fixed position.

12. The medical device system of claim 11, wherein when the first and second clips are releasably coupled with the first and second slots, the release wire is axially and rotatably secured relative to the elongate shaft.

13. The medical device system of claim 11, wherein when the first and second clips are disengaged from the first and second slots, the release wire is axially and rotatably movable relative to the elongate shaft.

14. The medical device system of claim 11, wherein proximal translation of the proximal portion of the securement member away from the proximal end of the elongate shaft translates the release wire axially relative to the elongate shaft.

15. The medical device system of claim 11, wherein the elongate shaft includes a first portion of a release mechanism attached to the distal end of the elongate shaft and the medical device includes a second portion of the release mechanism attached to a proximal end of the medical device;

wherein the release wire interlocks the first portion of the release mechanism with the second portion of the release mechanism when the proximal portion of the securement member is biased distally by a distal portion of the securement member.

\* \* \* \* \*